(12) United States Patent
Shai et al.

(10) Patent No.: US 9,072,441 B2
(45) Date of Patent: Jul. 7, 2015

(54) METHOD AND APPARATUS FOR IMAGING USING MULTIPLE IMAGING DETECTORS

(75) Inventors: Eyal Shai, Karkur (IL); Yaron Hefetz, Herzeliya (IL); Ira Micah Blevis, Zichron Yaakov (IL)

(73) Assignee: GE Medical Systems Israel, LTD., Tel Aviv (IL)

( * ) Notice: Subject to any disclaimer, the term of this patent is extended or adjusted under 35 U.S.C. 154(b) by 683 days.

(21) Appl. No.: 11/501,100

(22) Filed: Aug. 8, 2006

(65) Prior Publication Data
US 2008/0039721 A1 Feb. 14, 2008

(51) Int. Cl.
A61B 6/00 (2006.01)
A61B 6/03 (2006.01)
G01T 1/161 (2006.01)

(52) U.S. Cl.
CPC .............. *A61B 6/037* (2013.01); *A61B 6/032* (2013.01); *G01T 1/161* (2013.01); *A61B 6/4258* (2013.01); *A61B 6/501* (2013.01); *A61B 6/502* (2013.01); *A61B 6/541* (2013.01)

(58) Field of Classification Search
USPC ........................................................ 600/436
See application file for complete search history.

(56) References Cited

U.S. PATENT DOCUMENTS

| | | | |
|---|---|---|---|
| 4,181,939 A * | 1/1980 | Lyons | 378/4 |
| H12 H | 1/1986 | Bennett et al. | |
| 5,198,680 A | 3/1993 | Kurakake | |
| 5,431,161 A * | 7/1995 | Ryals et al. | 600/425 |
| 5,432,834 A | 7/1995 | Gershman | |
| 5,523,571 A | 6/1996 | Velazquez et al. | |
| 5,742,060 A * | 4/1998 | Ashburn | 250/370.09 |
| 5,757,006 A | 5/1998 | DeVito et al. | |
| 6,211,523 B1 * | 4/2001 | Gagnon | 250/363.04 |
| 6,242,743 B1 * | 6/2001 | DeVito et al. | 250/363.05 |
| 6,271,524 B1 | 8/2001 | Wainer et al. | |
| 6,583,420 B1 * | 6/2003 | Nelson et al. | 250/397 |
| 6,696,686 B1 * | 2/2004 | Wainer et al. | 250/363.1 |
| 6,946,660 B2 | 9/2005 | El-Hanany et al. | |
| 6,956,925 B1 | 10/2005 | Hoffman | |

(Continued)

FOREIGN PATENT DOCUMENTS

| WO | WO 2005 118 659 A2 | 12/2005 |
|---|---|---|
| WO | WO 2005 119 025 A2 | 12/2005 |

(Continued)

OTHER PUBLICATIONS

United States Statutory Invention Registration, Reg. No. H12, Published: Jan. 7, 1986, Inventors: Bennett et al., Assignee: The United States of America as represented by The United States Department of Energy, Washington, D.C., (13) pages.

*Primary Examiner* — Long V Le
*Assistant Examiner* — Farshad Negarestan
(74) *Attorney, Agent, or Firm* — Dean D. Small; The Small Patent Law Group, LLC

(57) ABSTRACT

An imaging system comprises a plurality of imaging detectors for acquiring imaging data. The plurality of imaging detectors is configurable to be arranged proximate to an anatomy of interest within a patient. Each of the plurality of imaging detectors has a field of view (FOV) and at least a portion of the plurality of imaging detectors image the anatomy of interest within the respective FOV. A processor receives the imaging data and processes the imaging data to form a multi-dimensional dataset having at least three dimensions.

23 Claims, 5 Drawing Sheets

(56) References Cited

U.S. PATENT DOCUMENTS

| | | | |
|---|---|---|---|
| 7,166,848 B2 | 1/2007 | El-Hanany et al. | |
| 7,208,740 B2 | 4/2007 | El-Hanany et al. | |
| 7,326,906 B2 | 2/2008 | Shalom et al. | |
| 7,339,176 B2 | 3/2008 | El-Hanany et al. | |
| 2004/0254464 A1* | 12/2004 | Stribling | 600/437 |
| 2005/0129295 A1 | 6/2005 | Shanmugam et al. | |
| 2005/0218331 A1 | 10/2005 | Blevis et al. | |
| 2005/0242292 A1 | 11/2005 | El-Hanany et al. | |
| 2006/0000978 A1* | 1/2006 | Engdahl et al. | 250/363.1 |
| 2006/0011852 A1 | 1/2006 | El-Hanany et al. | |
| 2006/0065840 A1* | 3/2006 | Joung et al. | 250/363.05 |
| 2007/0040126 A1 | 2/2007 | El-Hanany et al. | |
| 2007/0221853 A1* | 9/2007 | Joung | 250/363.09 |
| 2007/0278387 A1 | 12/2007 | Shalom et al. | |
| 2007/0295914 A1 | 12/2007 | El-Hanany et al. | |
| 2008/0149842 A1 | 6/2008 | El-Hanany et al. | |
| 2008/0237482 A1 | 10/2008 | Shahar et al. | |
| 2008/0277591 A1 | 11/2008 | Shahar et al. | |

FOREIGN PATENT DOCUMENTS

| | | |
|---|---|---|
| WO | WO 2006 051 531 A2 | 5/2006 |
| WO | WO 2006 054 296 A2 | 5/2006 |

* cited by examiner

METHOD AND APPARATUS FOR IMAGING USING MULTIPLE IMAGING DETECTORS

BACKGROUND OF THE INVENTION

This invention relates generally to Nuclear Medicine imaging systems, and more particularly, to applications for imaging systems having multiple small-size imaging detectors.

Various diagnostic imaging systems are used to view tissue and function of organs within a patient's body. Several challenges exist, such as technologies which create planar images rather than a three dimensional (3D) dataset, the inability to prevent interference from other areas of the body, and low resolution which inhibits detection of small lesions. Some procedures are painful for the patient due to equipment and/or having to remain still for an extended period of time.

Mammography is one technology which is frequently used to screen for and detect lesions in breast tissue using 2D images. Unfortunately, mammography is painful and has low detection efficiency in dense breasts. Scintillation-mammography, or scinti-mammography, uses a gamma camera to acquire 2D images of breast tissue, but is also painful and cannot detect lesions near the chest wall. The lesions are typically quite small, such as less than 0.5 cm in diameter, and produce low signal; the gamma camera may not provide the high sensitivity and high spatial resolution needed. Also, background radiation from organs within the torso can make detection more difficult.

The breasts may also be imaged using a multi-bore collimator and single photon emission computed tomography (SPECT), but the acquisition time is long and the images have low spatial resolution. Also, positron emission tomography (PET) is useful, but both the equipment and radioisotope are expensive and thus are not a viable option for routine use.

Brain imaging is not as common as breast imaging but has some of the same challenges as high resolution is required to detect small lesions. The level of resolution is beyond what is currently possible in SPECT using the multi-bore collimator.

Gated cardiac imaging is a common procedure used to image the heart. Gated SPECT is acquired using detector(s) having multi-bore collimators. The detectors are rotated around the patient and views are acquired at multiple positions, for example, 90 views over 180 degrees. Each view is typically acquired for at least ten seconds, and the gamma camera may be synchronized to the patient's ECG.

The views are divided into time sections relating to heart pulse motion. R waves are detected, and each R to R interval may be divided into 8 phases. Each phase is then reconstructed separately. If the heart beats are irregular, it may not be possible to determine the R to R interval accurately and the gated data is discarded. If enough valid beats are not acquired, any reconstructed data may be incomplete, of poor quality, and/or result in artifacts.

Cardiac creep, the physiological motion of the heart after stress, also causes problems for conventional cardiac gamma camera acquisitions. As the detector rotates over time and acquires images from different directions, the heart slowly moves. Artifacts may be created in the image as the position of the heart in the first and last images is different. These artifacts may erroneously appear to be a defect when the problem is actually motion over time.

Therefore, a need exists for method and apparatus to image desired structures of interest in less time and with less pain than currently available techniques, while also providing improved resolution. Certain embodiments of the present invention are intended to meet these needs and other objectives that will become apparent from the description and drawings set forth below.

BRIEF DESCRIPTION OF THE INVENTION

In one embodiment, an imaging system comprises a plurality of imaging detectors for acquiring imaging data. The plurality of imaging detectors is configurable to be arranged proximate to an anatomy of interest within a patient. Each of the plurality of imaging detectors has a field of view (FOV) and at least a portion of the plurality of imaging detectors images the anatomy of interest within the respective FOV. A processor receives the imaging data and processes the imaging data to form a multi-dimensional dataset having at least three dimensions.

In another embodiment, a method for acquiring imaging data with a plurality of small-size imaging detectors comprises configuring at least a portion of the plurality of small-size imaging detectors to be proximate to a structure of interest within a patient. Each of the plurality of small-size imaging detectors has a FOV. The FOV of the at least a portion of the plurality of small-size imaging detectors is aimed to image at least a portion of the structure of interest and imaging data is acquired with the at least a portion of the plurality of small-size imaging detectors.

In another embodiment, a method for acquiring imaging data with a plurality of imaging detectors comprises configuring at least a portion of a plurality of imaging detectors to be proximate to a structure of interest within a patient. Each of the at least a portion of the plurality of imaging detectors has a pinhole collimator positioned proximate thereto and has a FOV. The FOV of the at least a portion of the plurality of imaging detectors is aimed to image at least a portion of the structure of interest, and imaging data is acquired with the at least a portion of the plurality of imaging detectors while the at least a portion of the plurality of imaging detectors remain stationary with respect to the patient. The imaging data from the at least a portion of the plurality of imaging detectors is processed to form at least one multi-dimensional dataset having at least three dimensions.

Figure 1:
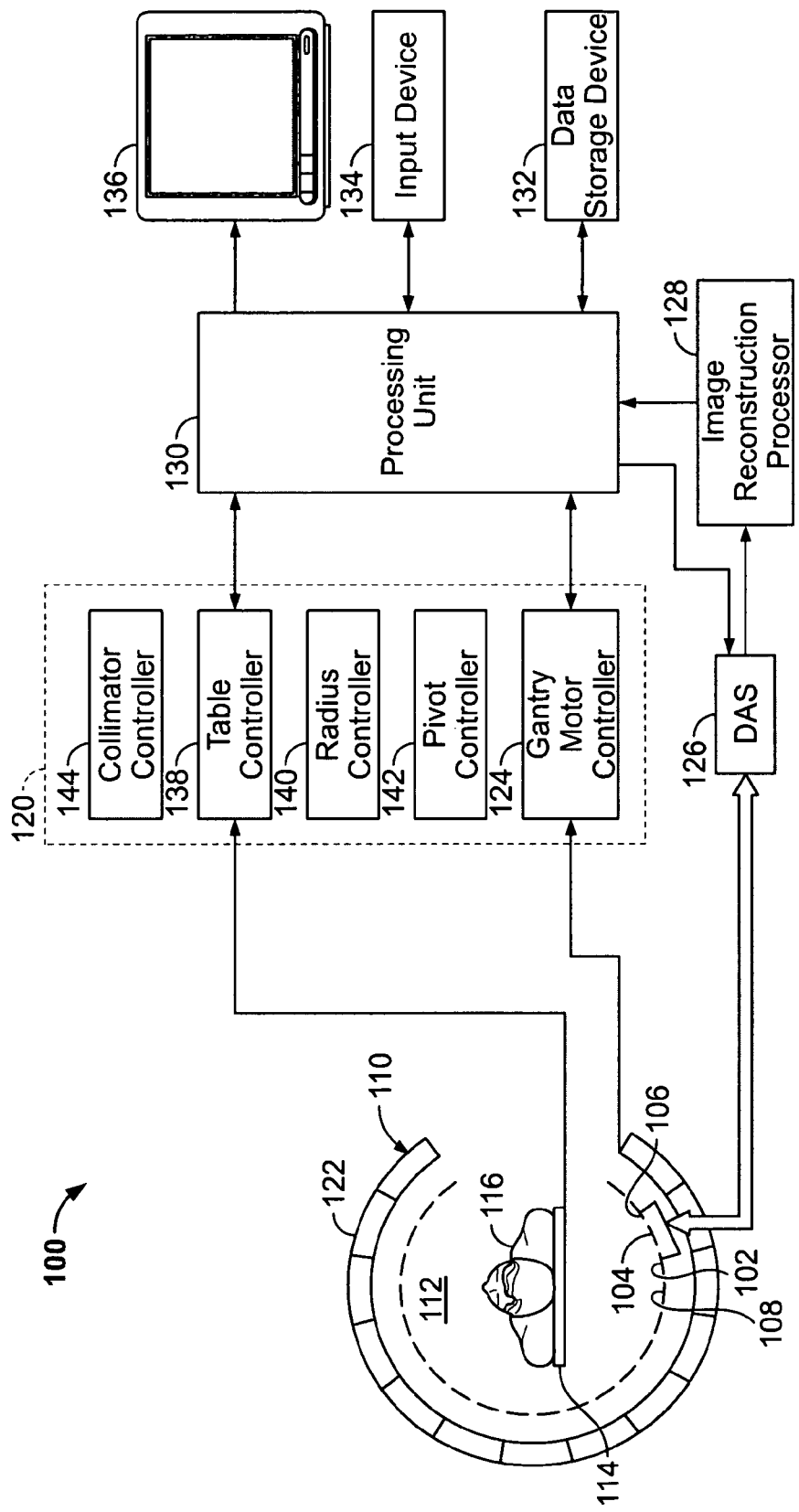
FIG. 1 is a schematic illustration of a Nuclear Medicine (NM) imaging system which has a plurality of small-sized imaging detectors mounted on a gantry formed in accordance with an embodiment of the present invention.

The foregoing summary, as well as the following detailed description of certain embodiments of the present invention, will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or a block or random access memory, hard disk, or the like). Similarly, the programs may be stand alone programs, may be incorporated as subroutines in an operating system, may be functions in an installed software package, and the like. It should be understood that the various embodiments are not limited to the arrangements and instrumentality shown in the drawings.

DETAILED DESCRIPTION OF THE INVENTION

FIG. 1 is a schematic illustration of a Nuclear Medicine (NM) imaging system 100 which has a plurality of small-sized imaging detectors mounted on a gantry. In FIG. 1, first, second, third through N imaging detectors 102, 104, 106 and 108 are mounted on a gantry 110. Each of the first through N imaging detectors 102-108 are smaller than a conventional imaging detector. A conventional imaging detector may be large enough to image most or all of a width of a patient's body at one time. For example, conventional imaging detectors may be rectangular in shape and approximately 18×40 cm and up to 40×54 cm in size. In contrast, each of the first through N imaging detectors 102-108 may have dimensions of 4 cm to 20 cm and may be formed of cadmium zinc telluride (CZT) tiles. For example, each of the first through N imaging detectors 102-108 may be 8×8 cm in size and be composed of a plurality of CZT pixilated modules (not shown) wherein each module may be 4×4 cm in size and have 16×16=256 pixels. It should be understood that the first through N imaging detectors 102-108 may be different sizes and/or shapes with respect to each other, such as square, rectangular, circular or other shape.

The gantry 110 may be formed with an aperture 112 therethrough as illustrated. A patient table 114 is configured with a support mechanism (not shown) to support and carry a patient 116 in a plurality of viewing positions within the aperture 112 and relative to the first through N imaging detectors 102-108. Alternatively, the gantry 110 may comprise a plurality of gantry segments 122, each of which may independently move one imaging detector or a subset of imaging detectors. The gantry 110 may also be configured in other shapes, such as a "C" and "L", and arranged to conform to an outline of a patient 116 or body part of interest. The gantry 110 may be formed as a closed ring or circle, or as an open arc or arch which allows the patient 116 to be easily accessed while imaging, facilitates loading and unloading the patient 116, as well as reduces claustrophobia in susceptible patients 116. The gantry 110 may be rotatable about the patient 116.

Also, additional imaging detectors may be positioned to form more than one arc or ring around the patient 116, or to focus imaging emphasis on particular anatomy. Optionally, imaging detectors may be arranged around the patient 116 in closed pack formation. Optionally, imaging detectors are arranged around the patient 116 in a plurality of axial locations.

Alternatively, the first through N imaging detectors 102-108 may be mounted on a pole or other support device(s) and a gantry may not be needed. Also, the patient 116 may sit on a stool, chair, or other support structure than the patient table 114, and thus may be imaged in an upright or reclined position.

It should be understood that different quantities of imaging detectors may be used. By positioning multiple imaging detectors at multiple positions with respect to the patient 116, radiation imaging data specific to a structure of interest within the patient 116 may be acquired more quickly compared to acquisitions using conventional large size detectors which also image areas that are not of interest and typically are rotated about the patient 116 in order to acquire the data needed for three-dimensional (3D) and four-dimensional (4D) (3D over time) dataset reconstruction.

Each of the first through N imaging detectors 102-108 has a radiation detection face (not shown) which is covered by a collimator (not shown) and directed towards a structure of interest within the patient 116. Depending upon the application, different types of collimators may be used, such as pinhole, parallel-beam converging or diverging fan-beam, and converging or diverging cone-beam type collimators. A field of view (FOV) of each of the first through N imaging detectors may be increased or decreased based on the collimator type. By way of example, a collimator may be mounted on or held proximate to each of the first through N imaging detectors 102-108. Alternatively, a mechanical structure (not shown) may hold all pinholes within one or more surfaces (rather than separate collimators) and the imaging detectors in relation to one another.

A controller unit 120 may control the movement and positioning of the patient table 114, the gantry 110, the first through N imaging detectors 102-108, and the collimators with a table controller 138, gantry motor controller 124, radius controller 140, pivot controller 142, and collimator controller 144, respectively. The individual controllers within the controller unit 120 may be automatically commanded by a processing unit 130, manually controlled by an operator, or a combination thereof. The gantry motor controller 124 may rotate the first through N imaging detectors 102-108 with respect to the patient 116 individually, according to interconnection with the gantry segments 122, or simultaneously in a fixed relationship to one another. Optionally, a mechanical link or links (not shown) may interconnect and move a plurality of imaging detectors in unison. The radius controller 140 may move each of the first through N imaging detectors 102-108 closer to and further from a surface of the patient 116, and the pivot controller 142 may move the first through N imaging detectors 102-108 axially with respect to the patient 116. The collimator controller 144 may adjust a position of an adjustable collimator, such as a collimator with adjustable strips (or vanes) or adjustable pinhole(s). It should be noted that motion of imaging detectors may be at directions other than strictly axially or radially. Optionally, motions in several motion directions are combined to create the desired motion.

Prior to acquiring an image of the structure of interest, the first through N imaging detectors 102-108 may be configured and adjusted to image all or a portion of the structure of interest within the FOV depending on the size of the structure, area(s) of greater interest within the structure, position of the structure within the patient 116, and the like. Alternatively, one or more of the first through N imaging detectors 102-108 may be idle while a portion or subset of the imaging detectors acquire imaging data.

After the first through N imaging detectors 102-108, gantry 110, patient table 114, and collimators are positioned, one or more images are acquired by each imaging detector being used. The image data acquired by each imaging detector may be combined and reconstructed into composite image(s), such as to form 2D images, and/or 3D, 4D or greater dataset(s) that may be displayed on a display 136. For example, a 5D dataset may be formed having three spatial dimensions as well as data acquired representative of time (e.g. Dynamic) and phase (e.g. Gated). Additional and/or other dimensions may be used. Also, an input device 134 may be provided, such as, to receive a user input.

A data acquisition system (DAS) 126 receives the electrical signal data produced by the first through N imaging detectors 102-108 and converts the data into digital signals, if necessary, for subsequent processing. An image reconstruction processor 128 and a data storage device 132 may also be provided. Although illustrated separately on FIG. 1, it should be noted that one or more functions related to one or more of data acquisition, motion control, data processing and image reconstruction may be accomplished in software and by shared processing resources.

Figure 2:
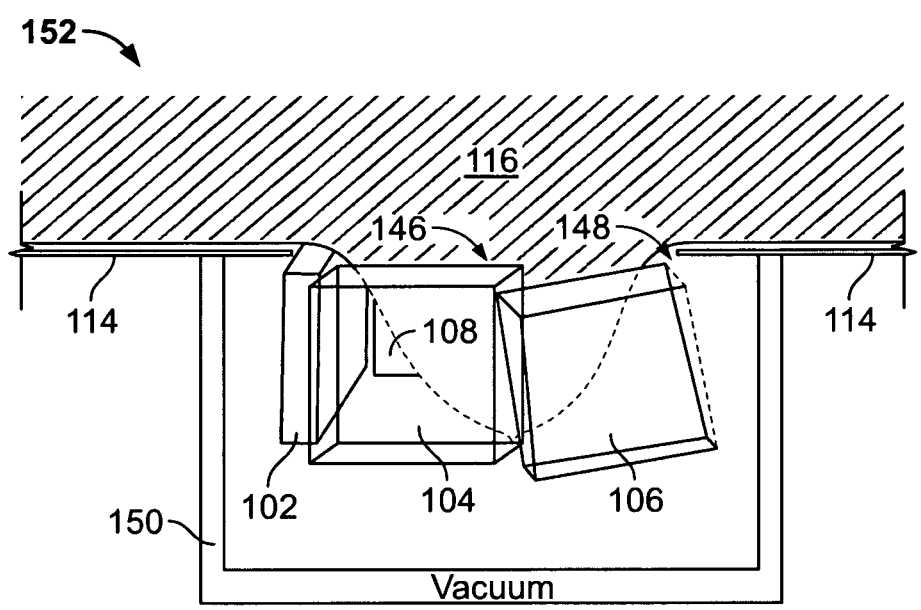
FIG. 2 illustrates a configuration of the imaging detectors of FIG. 1 which are positioned for breast imaging in accordance with an embodiment of the present invention.

FIG. 2 illustrates a configuration 152 of the first through N imaging detectors 102-108 of FIG. 1 which are positioned for breast imaging. The patient 116 may lay prone or face-down on the patient table 114 allowing breasts 146 to hang and/or extend through opening 148 in the patient table 114. Optionally, a vacuum device 150 may be used to exert a pulling force on the breasts 146. Alternatively, the patient 116 may be positioned in an upright position.

The first through N imaging detectors 102-108 may be arranged in an arc or hemisphere configuration to position the first through N imaging detectors 102-108 close to the breast 146. The collimators (not shown) may be pinhole or other type of collimator. The first through N imaging detectors 102-108 may be separately positioned such that each imaging detector is aimed to image a desired FOV, the entire breast 146, or a portion of the breast 146. Therefore, most of the background radiation coming from the organs within the patient's torso may be avoided. The first through N imaging detectors 102-108 may be stationary during the acquisition, or may move with respect to the patient 116, such as to image a larger FOV. The breast 146 may thus be imaged without compression, as used in mammography. Also, as multiple images from different directions are acquired simultaneously, the time the patient 116 needs to remain motionless is minimized.

Figure 3:
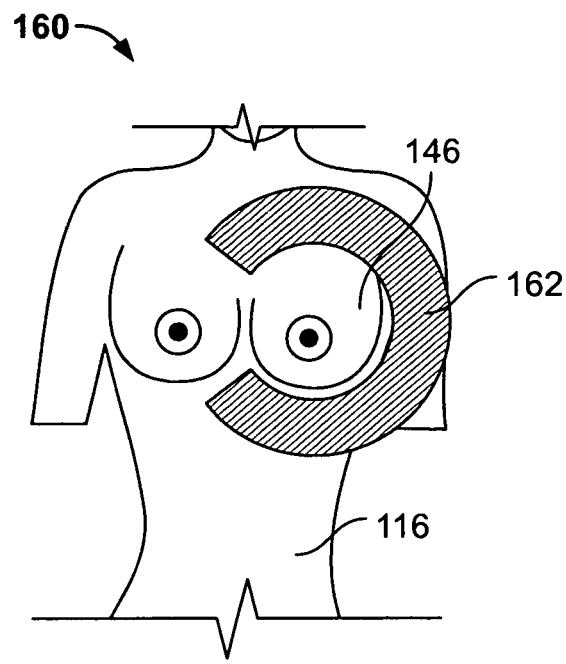
FIG. 3 illustrates a view of a configuration for imaging a single breast with the imaging system of FIG. 1 in accordance with an embodiment of the present invention.

FIG. 3 illustrates a view of a configuration 160 for imaging a single breast 146 with the imaging system 100 of FIG. 1. The configuration 160 may be utilized having the patient 116 in either the prone or upright position. A desired number of the first through N imaging detectors 102-108 are arranged in an arc 162 about the breast 146 of the patient 116. Because the first through N imaging detectors 102-108 are small in size, the first through N imaging detectors 102-108 may be positioned close to the patient 116 and each may be individually aimed and adjusted to detect radiation from slightly different directions with respect to each other to achieve the desired FOV. As there is no need to rotate the first through N imaging detectors 102-108 about the breast 146, the scan time is reduced compared to scanning with a traditional SPECT system. Also, no uncomfortable compression of the breast tissue is needed.

Figure 4:
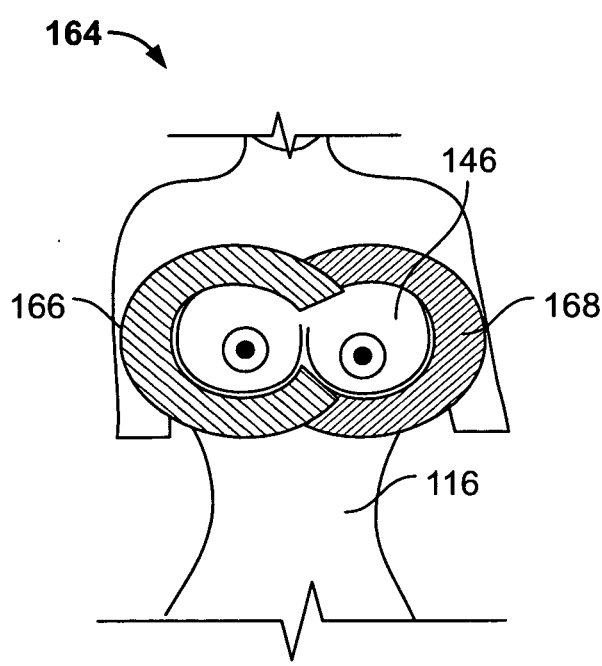
FIG. 4 illustrates a view of a configuration for imaging both breasts of a patient at the same time with the imaging system of FIG. 1 in accordance with an embodiment of the present invention.

FIG. 4 illustrates a view of a configuration 164 for imaging both breasts 146 at the same time with the imaging system 100 of FIG. 1. The desired number of the first through N imaging detectors 102-108 are arranged in first and second arcs 166 and 168 about the breasts 146. By imaging both breasts 146 at the same time, the total scan time for the patient 116 may be greatly reduced and/or a greater amount of imaging data may be acquired.

Figure 5:
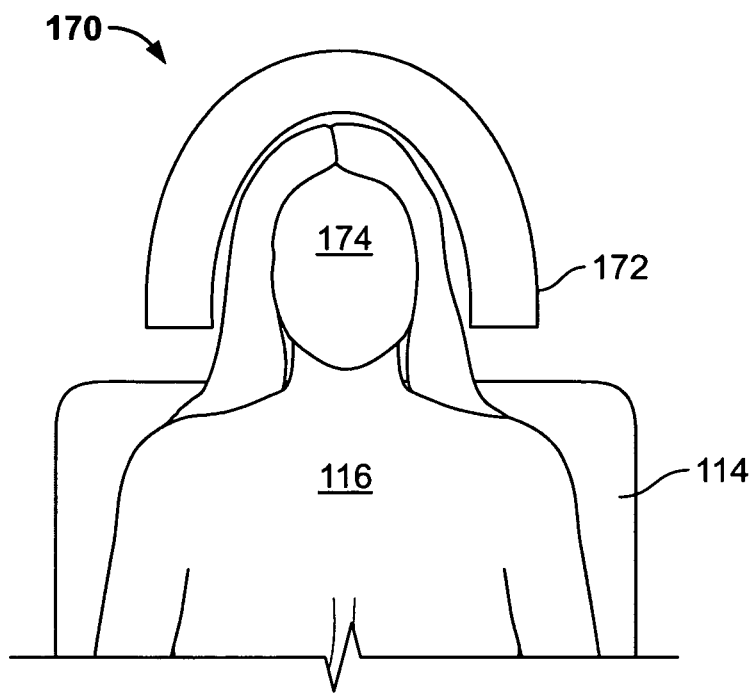
FIG. 5 illustrates a view of a configuration for using the imaging system of FIG. 1 to image structures within the patient's head in accordance with an embodiment of the present invention.

FIG. 5 illustrates a view of a configuration 170 for using the imaging system 100 of FIG. 1 to image structures within the patient's head. The patient 116 may be positioned prone or supine on the patient table 114, or may be seated upright. The first through N imaging detectors 102-108 may be arranged in an arc 172 similar to the configurations 152, 160 and 164 discussed in FIGS. 2-4. Optionally, the first through N imaging detectors 102-108 may be positioned to form an inner cup portion (not shown), encircling at least a portion of the head 174 in a helmet-like fashion. The first through N imaging detectors 102-108 are aimed to achieve the desired FOV, and may be stationary or may move with respect to the patient 116 during the acquisition. Pinhole collimators may be used to further direct the FOV to image the brain or other structures within the head 174.

Figure 6:
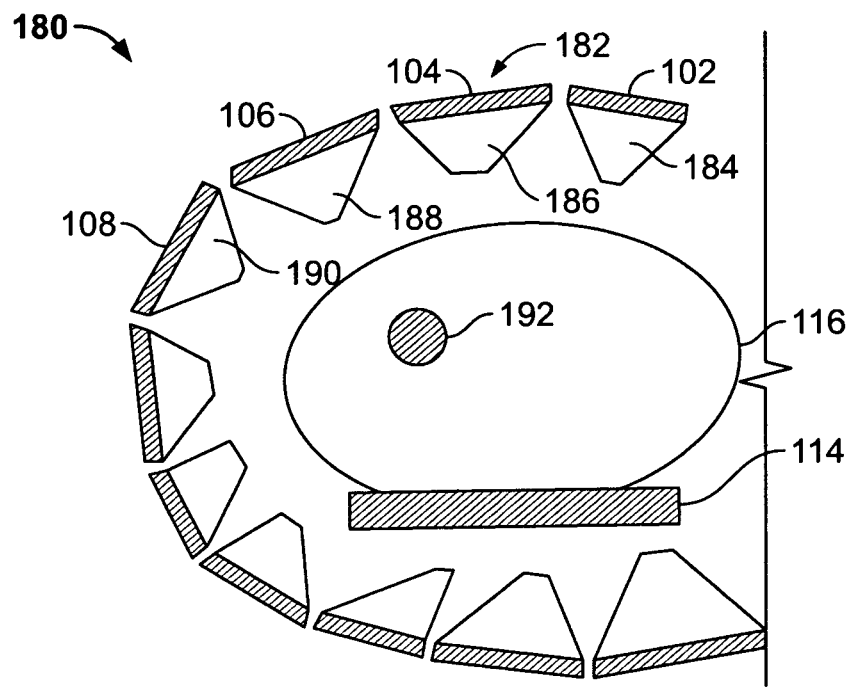
FIG. 6 illustrates a view of a configuration for cardiac imaging wherein the imaging detectors of the imaging system (FIG. 1) are arranged relatively evenly about the patient in accordance with an embodiment of the present invention.

FIG. 6 illustrates a view of a configuration 180 for cardiac imaging wherein the first through N imaging detectors 102-108 of the imaging system 100 (FIG. 1) are arranged relatively evenly about the patient 116. The first through N imaging detectors 102-108 are arranged in an arc 182 around the torso of the patient 116. Each of the first through N imaging detectors 102, 104, 106 and 108 has first, second, third through N pinhole collimator 184, 186, 188 and 190, respectively, mounted thereon or positioned relative thereto. The first through N pinhole collimators 184-190 may be adjusted by the collimator controller 144 to view desired portions or all of heart 192. Alternatively, the first through N pinhole collimators 184-190 and the first through N imaging detectors 102-108 may be positioned such that the imaging detectors are positioned in the FOV of the pinholes.

Figure 7:
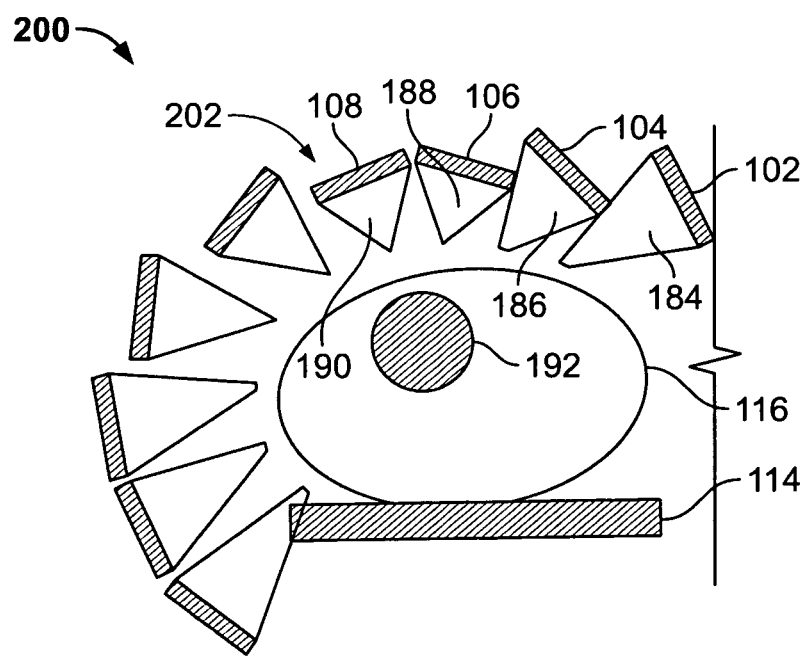
FIG. 7 illustrates a view of a configuration for cardiac imaging wherein the imaging detectors of the imaging system (FIG. 1) are arranged unevenly about the patient in accordance with an embodiment of the present invention.

FIG. 7 illustrates a view of a configuration 200 for cardiac imaging wherein the first through N imaging detectors 102-108 of the imaging system 100 (FIG. 1) are arranged unevenly about the patient 116. The first through N imaging detectors 102-108 are arranged generally in an arc 202 around the torso of the patient 116. The first through N imaging detectors 102-108 may have the first through N pinhole collimators 184-190 mounted thereon and are positioned to view the heart 192.

Although the single arcs 182 and 202 of imaging detectors are illustrated in FIGS. 6 and 7, the first through N imaging detectors 102-108 may be configured in two or more arcs 182 and 202. Each arc may span, for example, 90 to 270 degrees around the patient 116 to image a substantial portion of the torso. For example, three such arcs, using 8×8 cm size imaging detectors as discussed in FIG. 1 may form a curved band having at least a 24 cm width.

The configurations 180 and 200 of FIGS. 6 and 7 may be used for a number of cardiac applications in which it is advantageous to acquire multiple views of the heart 192 quickly over a short period of time. In Dynamic/First Pass SPECT imaging, a bolus of radiolabeled liquid is imaged during its first pass through the heart 192, which takes only a few seconds. Using previous imaging systems, a set of time-gated planar (2D) images are acquired as no rotating gamma camera is fast enough to take a succession of images during the short time. The imaging system 100, however, acquires time-gated datasets wherein each dataset has a complete set of views from all around the heart 192. Therefore, a sequence of 3D datasets or images may be reconstructed.

Figure 8:
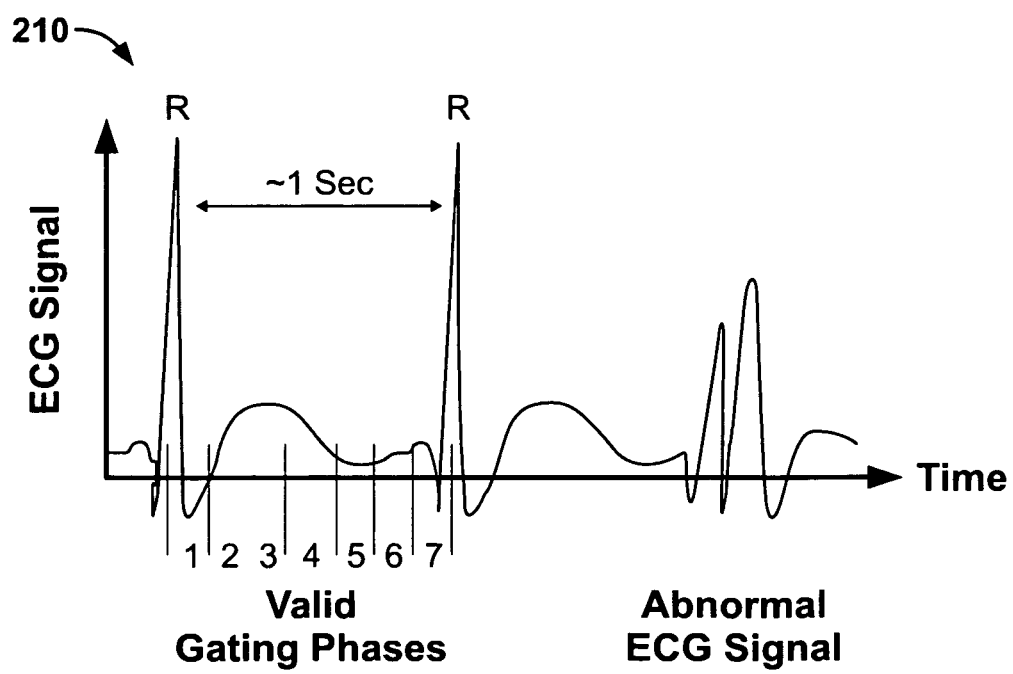
FIG. 8 illustrates an ECG signal over time in accordance with an embodiment of the present invention.

Cardiac gated SPECT may similarly be acquired. FIG. 8 illustrates an ECG signal 210 over time. Gated cardiac images may be acquired in a much shorter time period compared to previous rotating cameras, and may allow acquisition of more data over a shorter time period to compensate for a heart 192 having many irregular beats.

Heart creep may interfere with image reconstruction as discussed previously. However, with the configurations of FIGS. 6 and 7, an entire cardiac scan is completed in a much shorter time period, such as three minutes, and the heart creep after exercise may be negligible. As the first through N imaging detectors 102-108 are stationary and do not move to acquire the views, any creep motion that occurs is equally registered in all views and thus may be averaged to negate the reconstruction artifacts previously experienced.

Alternatively, datasets may be divided into sub-groups, such as three one-minute sub-groups. Each sub-group is imaged in an almost constant phase of the heart creep. Each sub-group is reconstructed separately, the images are co-registered, such as by rigid body translation/rotations or by "morphing", and added to form the final image.

Using traditional cardiac SPECT, perfusion defects within the heart 192 are identified by reduction in activity compared to regions in the heart 192 with normal perfusion, which assumes that there are normal regions in the heart. In the case of Three Vessel Disease, or balanced ischemia, this assumption is not valid as there is decreased perfusion in the entire left ventricle. Balanced ischemia is one of the main reasons for false negative cardiac SPECT scans.

Coronary flow reserve is a quantitative index that may be used to differentiate Three Vessel Disease from normal myocardium. A dynamic acquisition is required, and therefore requires an imaging system capable of quickly acquiring the data. When imaging a dynamic process such as the flow of blood to the left ventricle, it is advantageous to acquire data without moving the detectors. The imaging system 100 can accommodate both of these requirements.

It should be understood that other anatomy may be imaged. For example, the first through N imaging detectors 102-108 may be arranged in a planar configuration to acquire a 2D image of an abdomen. Alternatively, each of the first through N imaging detectors 102-108 may be arranged to acquire data from multiple anatomy simultaneously.

A technical effect is the ability to configure a plurality of small-size imaging detectors to more efficiently image a structure of interest. The imaging detectors are arranged to view the structure from different directions, such as forming one or more arc around a breast or the torso of a patient. The imaging data may be acquired more quickly with little or no need for movement of the imaging detectors.

While the invention has been described in terms of various specific embodiments, those skilled in the art will recognize that the invention can be practiced with modification within the spirit and scope of the claims.

What is claimed is:

1. An imaging system, comprising:
   a gantry;
   a plurality of imaging detectors for acquiring imaging data, each of the imaging detectors having a length and a width of 20 cm or less, the plurality of imaging detectors mounted to the gantry and configurable to be arranged proximate to an anatomy of interest within a patient, the plurality of imaging detectors configured to move together in a circumferential path about the patient with the gantry when the gantry rotates about the patient and to be individually positionable to focus on the anatomy of interest when the gantry is stationary;
   a plurality of corresponding pinhole collimators, each pinhole collimator mounted or positioned proximate to one of the plurality of imaging detectors to define a field of view (FOV) for each imaging detector, at least a portion of the plurality of imaging detectors imaging the anatomy of interest within the respective FOV;
   a processor receiving the imaging data and processing the imaging data to form a multi-dimensional dataset having at least three dimensions; and
   a controller unit configured to control at least one of the plurality of imaging detectors or the plurality of pinhole collimators to individually focus the plurality of imaging detectors on the anatomy of interest, the controller unit further configured to control rotation of the plurality of imaging detectors with the gantry to a plurality of rotation positions about the patient, wherein, while the gantry is stationary at one of the rotation positions, the controller unit individually positions the at least one of the plurality of imaging detectors or the plurality of pinhole collimators about the anatomy of interest to acquire the imaging data while the imaging detectors are stationary, wherein the controller is configured to individually position the at least one of the plurality of imaging detectors by rotating the at least one of the plurality of imaging detectors about an axis that is parallel to an axis about which the gantry is configured to be rotated.

2. The system of claim 1, wherein the controller unit is configured to individually position the plurality of imaging detectors in at least one of at least one arc and at least one circle proximate to the anatomy of interest while the gantry is stationary.

3. The system of claim 1, wherein the anatomy of interest is one of a breast, a heart, or a brain, the plurality of imaging detectors being arranged in at least one arc to at least partially encircle the breast, torso, and head, respectively, of the patient.

4. The system of claim 1, wherein the plurality of imaging detectors are arranged in at least one arc proximate to the anatomy of interest, the plurality of imaging detectors being one of evenly or unevenly positioned with respect to each other.

5. The system of claim 1, wherein the anatomy of interest is one of a brain or a heart.

6. The system of claim 1, wherein the anatomy of interest is a breast of the patient and further comprising a vacuum device to exert a pulling force on the breast.

7. The system of claim 1, wherein the anatomy of interest are human breasts and wherein the plurality of imaging detectors comprise first and second arcs each configured to surround and image a different breast concurrently.

8. The system of claim 1, wherein the plurality of imaging detectors and pinhole collimators are stationary and focused on the anatomy of interest during an entire image acquisition process at one of different positions of the plurality of imaging detectors.

9. The system of claim 1, wherein the controller is further configured to control at least one of the movement or the positioning of the plurality of imaging detectors to move one or more of the imaging detectors closer to or farther away from the patient.

10. The system of claim 1, wherein the controller is further configured to control at least one of the movement or the positioning of the plurality of imaging detectors to one of pivot or rotate more than one of the imaging detectors while the gantry is stationary.

11. The system of claim 1, wherein the gantry is configured to rotate at least 45 degrees about the patient.

12. The system of claim 1, wherein the controller is further configured to control at least one of the movement or the positioning of the plurality of imaging detectors to move one or more of the imaging detectors in a plurality of motion directions to create a desired combined motion.

13. A method for acquiring imaging data with a plurality of small-size imaging detectors, comprising:
configuring at least a portion of a plurality of small-size imaging detectors to be proximate to a structure of interest within a patient and conform to the patient, wherein the plurality of small-size imaging detectors form separate imaging units, each of the small-size imaging detectors having a length and a width of 20 cm or less;
mounting or positioning proximate to each of the plurality of small-size imaging detectors a pinhole collimator to define a field of view (FOV) for each imaging detector;
individually aiming the FOV of the at least a portion of the plurality of small-size imaging detectors while a gantry to which the small-size detectors are mounted is stationary to acquire imaging data of the structure of interest, wherein the FOV of the at least a portion of the plurality of small-size imaging detectors is individually aimed by rotating the at least a portion of the plurality of small-size imaging detectors individually about an axis that is parallel to an axis about which the gantry is configured to be rotated; and
acquiring imaging data with the at least a portion of the plurality of small-size imaging detectors while the gantry is stationary.

14. The method of claim 13, further comprising positioning the plurality of small-size imaging detectors in one of a ring, an arc, more than one ring, or more than one arc proximate to the structure of interest within the patient while the gantry is stationary.

15. The method of claim 13, wherein the structure of interest further comprises at least one breast, the method further comprising aiming the FOV of at least a portion of the plurality of small-sized imaging detectors to image at least a portion of the at least one breast.

16. The method of claim 13, further comprising:
positioning the plurality of small-size imaging detectors to be at least partially within the FOV of the pinhole collimators.

17. A method for acquiring imaging data with a plurality of imaging detectors, comprising:
configuring at least a portion of a plurality of nuclear medicine imaging detectors to be proximate to a structure of interest within a patient, each of the at least a portion of the plurality of imaging detectors having a pinhole collimator positioned proximate thereto and having a field of view (FOV), the imaging detectors mounted to a gantry with which the imaging detectors are configured to rotate to a plurality of rotation positions, each of the imaging detectors having a length and a width of 20 cm or less;
individually aiming, with a control unit, the FOV of the at least a portion of the plurality of imaging detectors while a gantry to which the imaging detectors are mounted is stationary at one of the rotation positions to acquire imaging data, wherein the FOV of the at least a portion of the plurality of imaging detectors is individually aimed by rotating the at least a portion of the plurality of imaging detectors individually about an axis that is parallel to an axis about which the gantry is configured to be rotated;
acquiring imaging data with the at least a portion of the plurality of imaging detectors while the gantry is stationary; and
processing the imaging data from the at least a portion of the plurality of imaging detectors to form at least one multi-dimensional dataset having at least three dimensions using imaging data acquired only at the one of the rotation positions.

18. The method of claim 17, further comprising positioning the at least a portion of the plurality of imaging detectors in at least one of at least one arc or at least one circle proximate to the anatomy of interest.

19. The method of claim 17, wherein the anatomy of interest is the heart, the method further comprising acquiring first through N sub-sets of imaging data over time, each sub-set comprising imaging data from the at least a portion of the plurality of imaging detectors.

20. The method of claim 17, wherein the pinhole collimators are adjustable pinhole collimators, the method further comprising adjusting at least one of the adjustable pinhole collimators to change the FOV of at least one of the plurality of imaging detectors.

21. The method of claim 17, wherein the structure of interest is a heart, the method further comprising acquiring gated imaging data.

22. The method of claim 17, wherein the structure of interest is a heart, the method further comprising acquiring dynamic imaging data.

23. An imaging system, comprising:
a gantry configured for rotation about a patient;
a plurality of imaging detectors for acquiring imaging data, the plurality of imaging detectors mounted to the gantry and configurable to be arranged proximate to an anatomy of interest within a patient, the plurality of imaging detectors configured to move together in a circumferential path about the patient with the gantry when the gantry rotates about the patient, the plurality of imaging detectors individually positionable to aim a field of view (FOV) of at least some of the imaging detectors to focus on the anatomy of interest when the gantry is stationary, each of the imaging detectors having a length and a width of 20 cm or less;
a plurality of corresponding pinhole collimators, each pinhole collimator mounted or positioned proximate to one of the plurality of imaging detectors to define the FOV for each of the imaging detectors;
a controller unit configured to control at least one of the plurality of imaging detectors or the plurality of pinhole collimators to individually focus the at least some of imaging detectors on the anatomy of interest, the controller unit further configured to control rotation of the plurality of imaging detectors with the gantry to a plurality of rotation positions about the patient, wherein, while the gantry is stationary at one of the rotation positions, the controller unit individually positions the at least some of the imaging detectors about the anatomy of interest and focuses the at least some of the imaging detectors on the anatomy of interest to acquire the imaging data while the imaging detectors are stationary, wherein the controller is configured to individually position the at least one of the plurality of imaging detectors by rotating the at least one of the plurality of imaging detectors about an axis that is parallel to an axis about which the gantry is configured to be rotated; and at least one processing unit configured to receive the imaging data acquired while the imaging detectors are stationary at the one of the rotation positions and to reconstruct an image using only the imaging data that was acquired while the imaging detectors are stationary at the one of the rotation positions.

\* \* \* \* \*